US00PP18152P2

(12) United States Plant Patent
Kabbes

(10) Patent No.: US PP18,152 P2
(45) Date of Patent: Oct. 30, 2007

(54) ***SALVIA* PLANT NAMED 'PINK FRIESLAND'**

(50) Latin Name: *Salvia nemorosa*
Varietal Denomination: Pink Friesland

(76) Inventor: Brian Kabbes, Jelke Sjoerdlaan 4, 9262 SL Suameer (NL)

( * ) Notice: Subject to any disclaimer, the term of this patent is extended or adjusted under 35 U.S.C. 154(b) by 0 days.

(21) Appl. No.: 11/450,827

(22) Filed: Jun. 9, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Salvia* plant named 'Pink Friesland', characterized by its upright and relatively compact plant habit; freely basal branching, dense and bushy plant form; freely flowering habit; pink-colored flowers; and tolerance to low temperatures.

1 Drawing Sheet

Botanical designation: *Salvia nemorosa.*
Cultivar denomination: 'Pink Friesland'.

BACKGROUND OF THE INVENTION

The present invention relates to a new and distinct cultivar of *Salvia,* botanically known as *Salvia nemorosa* and hereinafter referred to by the name 'Pink Friesland'.

The new *Salvia* is a product of a planned breeding program conducted by the Inventor in Suameer, The Netherlands. The objective of the breeding program is to create new compact and freely branching *Salvia* cultivars with numerous attractive flowers and good garden performance.

The new *Salvia* originated from a cross-pollination made by the Inventor in 2002 of a proprietary selection of *Salvia nemorosa* identified as code number 98-43-01, not patented, as the female, or seed, parent with a proprietary selection of *Salvia nemorosa* identified as code number 01-14-06, not patented, as the male, or pollen, parent. The new *Salvia* was discovered and selected by the Inventor as a single flowering plant with the progeny of the stated cross-pollination grown in a controlled environment in Suameer, The Netherlands in 2003.

Asexual reproduction of the new cultivar by vegetative cuttings in Suameer, The Netherlands, since 2004, has shown that the unique features of this new *Salvia* are stable and reproduced true to type in successive generations.

SUMMARY OF THE INVENTION

Plants of the cultivar Pink Friesland have not been observed under all possible environmental conditions. The phenotype may vary somewhat with variations in environment such as temperature and light intensity without, however, any variance in genotype.

The following traits have been repeatedly observed and are determined to be the unique characteristics of 'Pink Friesland'. These characteristics in combination distinguish 'Pink Friesland' as a new and distinct cultivar:

1. Upright and relatively compact plant habit.
2. Freely basal branching, dense and bushy plant form.
3. Freely flowering habit.

4. Pink-colored flowers.
5. Tolerant to low temperatures.

Plants of the new *Salvia* differ from plants of the female parent selection in the following characteristics:

1. Plants of the new *Salvia* are more compact than plants of the female parent selection.
2. Plants of the new *Salvia* and the female parent selection differ in flower color as plants of the female parent selection have red-colored flowers.

Plants of the new *Salvia* differ from plants of the male parent selection in the following characteristics:

1. Plants of the new *Salvia* are more compact than plants of the male parent selection.
2. Plants of the new *Salvia* and the male parent selection differ in flower color as plants of the male parent selection have blue-colored flowers.

Plants of the new *Salvia* can be compared to plants of the cultivar Marcus, not patented. In side-by-side comparisons conducted by the Inventor in Suameer, The Netherlands, plants of the new *Salvia* differed from plants of the cultivar Marcus in the following characteristics:

1. Plants of the new *Salvia* were more freely branching than plants of the cultivar Marcus.
2. Plants of the new *Salvia* had stronger flowering stems than plants of the cultivar Marcus.
3. Plants of the new *Salvia* and the cultivar Marcus differed in flower color as plants of the cultivar Marcus had purple-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Salvia.* The photograph comprises a side perspective view of a typical flowering plant of 'Pink Friesland' grown in a container.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photograph and following description were grown under conditions which closely approximate commercial production conditions during the spring and summer in an outdoor nursery in Aalsmeer, The Netherlands for about three months after planting in containers. During the production of the plants, day temperatures averaged 22° C. and night temperatures averaged 14° C. Plants were pinched one time about two weeks after planting.

Botanical classification: *Salvia nemorosa* cultivar Pink Friesland.

Parentage:

*Female parent.*—Proprietary selection of *Salvia nemorosa* identified as code number 98-43-01, not patented.

*Male parent.*—Proprietary selection of *Salvia nemorosa* identified as code number 01-14-06, not patented.

Propagation:

*Type cutting.*—Vegetative cuttings.

*Time to initiate roots.*—About two weeks at 22° C.

*Time to produce a rooted young plant.*—About four weeks at 22° C.

*Root description.*—Fine, freely branching; white in color.

Plant description:

*Form.*—Upright and relatively compact plant form. Freely basal branching with about ten main stems; dense and bushy plant habit; moderately vigorous growth habit. Flowers arranged in verticillasters on spikes.

*Plant height.*—About 20 cm to 50 cm.

*Plant width.*—About 20 cm to 30 cm.

*Lateral branch description.*—Length: About 10 cm. Diameter: About 4 mm to 6 mm. Internode length: About 2 cm. Strength: Strong. Aspect: Mostly upright to slightly outwardly spreading. Texture: Smooth, glabrous. Color: 143C.

Foliage description:

*Arrangement.*—Opposite, simple.

*Length.*—About 6 cm.

*Width.*—About 2 cm.

*Shape.*—Narrowly deltoid.

*Apex.*—Sharply acute.

*Base.*—Obtuse.

*Margin.*—Serrate.

*Texture, upper and lower surfaces.*—Smooth, glabrous.

*Venation pattern.*—Pinnate.

*Color.*—Developing and fully expanded foliage, upper surface: 143A; venation, 139D. Developing and fully expanded foliage, lower surface: 143C; venation, 139D.

*Petiole length.*—About 2 cm.

*Petiole diameter.*—About 1 mm.

*Petiole texture, upper and lower surfaces.*—139D.

*Petiole color, upper and lower surfaces.*—139C.

Flower description:

*Flower arrangement and shape.*—Single bilabiate flowers in verticillasters on spikes; flowers face mostly outwardly. Freely flowering, about 100 flowers per inflorescence.

*Natural flowering season.*—Continuous flowering from July through September in The Netherlands.

*Flower longevity on the plant.*—About two weeks; flowers persistent.

*Flower buds.*—Length: About 5 mm. Diameter: About 2 mm to 3 mm. Shape: Oblong. Color: 64C.

*Inflorescence size.*—Length: About 10 cm to 20 cm. Diameter: About 3 cm.

*Flowers.*—Diameter: About 5 mm. Depth (height): About 1.5 mm.

*Petals.*—Arrangement: Two, fused at the base. Length: About 1 cm. Width: About 5 mm. Shape: Oblong. Apex: Rounded. Margin: Entire. Texture, upper and lower surfaces: Smooth, glabrous. Color: When opening and fully opened, upper surface: 64C. When opening and fully opened, upper surface: 64C. When opening and fully opened, lower surface: 64C.

*Calyx.*—Shape: Two sepals fused into a tube. Length: About 5 mm. Width: About 3 mm to 4 mm. Texture, upper and lower surfaces: Smooth, glabrous. Color, upper and lower surfaces: Close to 144A.

*Peduncles.*—Strength: Strong. Length: About 30 cm Diameter: About 4 mm to 5 mm. Aspect: Mostly upright to slightly outwardly spreading. Texture: Smooth, glabrous. Color: 143A.

*Pedicels.*—Strength: Strong. Length: About 0.5 mm to 1 mm. Diameter: About 0.5 mm. Aspect: About 60° from the stem axis. Texture: Smooth, glabrous. Color: 185A.

*Reproductive organs.*—Stamens: Qauntity per flower: Five. Anther shape: Ovate. Anther length: About 1 mm. Anther color: Whitish green. Pollen amount: Abundant. Pollen color: Whitish. Pistils: Quantity per flower: One. Pistil length: About 5 mm. Stigma shape: Bi-lobed. Stigma color: 64C. Style length: About 1 mm to 1.5 mm. Style color: 64D. Ovary color: Close to 144B.

*Seed/fruit.*—Seed and fruit production has not been observed.

Disease/pest resistance: Plants of the new *Salvia* have not been noted to be resistant to pathogens and pests common to *Salvia,* however plants of the new *Salvia* have been observed to be tolerant to Powdery Mildew.

Garden performance: Plants of the new *Salvia* have exhibited good tolerance to rain and wind and have been observed to tolerate temperatures from about −20° C. to about 35° C.

It is claimed:

1. A new and distinct *Salvia* plant named 'Pink Friesland' as illustrated and described.

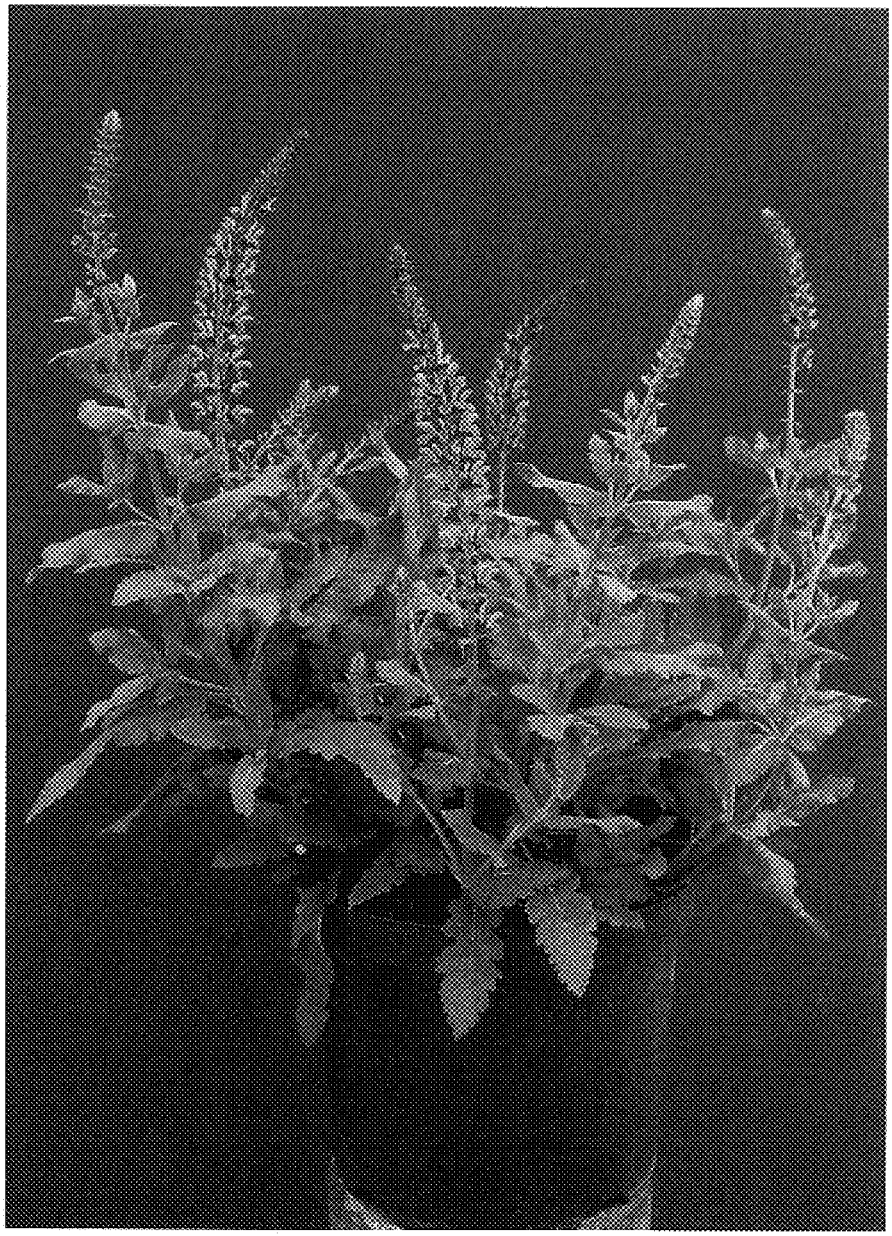

* * * * *